(12) United States Patent
Chu

(10) Patent No.: US 7,441,300 B2
(45) Date of Patent: *Oct. 28, 2008

(54) INTERDENTAL TOOTHBRUSH

(76) Inventor: Henry C. Chu, 133N. Lemon St., Orange, CA (US) 92866

( * ) Notice: Subject to any disclaimer, the term of this patent is extended or adjusted under 35 U.S.C. 154(b) by 0 days.

This patent is subject to a terminal disclaimer.

(21) Appl. No.: 11/715,061

(22) Filed: Mar. 6, 2007

(65) Prior Publication Data

US 2008/0216266 A1    Sep. 11, 2008

(51) Int. Cl.
*A46B 9/04* (2006.01)
(52) U.S. Cl. .................................... 15/167.1
(58) Field of Classification Search ............... 15/167.1
See application file for complete search history.

(56) References Cited

U.S. PATENT DOCUMENTS

| 4,395,943 A | 8/1983 | Brandli |
| 4,691,404 A | 9/1987 | Tarrson et al. |
| 5,309,596 A | 5/1994 | Simms |
| 5,488,751 A | 2/1996 | Gekhter et al. |
| 5,699,578 A * | 12/1997 | Dumler et al. ............. 15/167.1 |
| 5,862,559 A * | 1/1999 | Hunter .......................... 15/28 |

* cited by examiner

*Primary Examiner*—Randall Chin
(74) *Attorney, Agent, or Firm*—Charles E. Baxley

(57) ABSTRACT

An interdental toothbrush includes one or more wires having fixed filaments disposed on the wires, and a gage disposed on one end portion of the wires and having an outer diameter equal to or smaller than that of the filaments for limiting and guiding the wires and the filaments to engage into the predetermined or suitable or selected interdental spaces between the teeth of the user and for preventing the filaments from being inserted and engaged into the interdental spaces having a relatively smaller width and thus for preventing the user's gum from being hurt or injured by the greater filaments.

7 Claims, 2 Drawing Sheets

INTERDENTAL TOOTHBRUSH

BACKGROUND OF THE INVENTION

1. Field of the Invention

The present invention relates to an interdental toothbrush, and more particularly to an interdental toothbrush including a gage for guiding the interdental toothbrush to be inserted or engaged into the predetermined or suitable interdental spaces between the teeth and for preventing the interdental toothbrushes of greater sizes or diameters from being inserted or engaged into the interdental spaces having relatively smaller sizes or widths.

2. Description of the Prior Art

Typical interdental toothbrushes comprise one or more twisted wires having fixed filaments between turns of the wire or wires for inserting or engaging into the interdental spaces between the teeth and particularly designed for cleaning the hard-to-reach interdental spaces between the teeth of the users.

For example, U.S. Pat. No. 4,395,943 to Brandii discloses one of the typical interproximal toothbrushes also comprise one or more twisted wires having fixed filaments between turns of the wire or wires for inserting or engaging into the interdental spaces between the teeth, and an electrically insulated, wear-resistant and elastic layer applied onto the outer peripheral portion of the wire or wires.

Normally, in one package of the typical interproximal toothbrushes, two or more brushes or refills having different shapes or sizes or diameters may be provided, and the brushes or refills may be selected from such as the ultra fine cylindrical shapes, the ultra fine tapered shapes, the cylindrical shapes, the tapered shapes, the large cylindrical shapes, or the like.

However, when the interdental toothbrushes of greater sizes or diameters are forced to be inserted or engaged into the interdental spaces having relatively smaller sizes or widths, the gum of the user may be hurt or injured by the interdental toothbrushes. In addition, the twisted wires may also have a good chance to hurt or injure the gum of the user when the twisted wires of the interdental toothbrushes are not precisely engaged into the interdental spaces between the teeth.

U.S. Pat. No. 4,691,404 to Tarrson et al., U.S. Pat. No. 5,309,596 to Simms, and U.S. Pat. No. 5,488,751 to Gekhter et al. discloses three further typical interproximal toothbrushes each comprise a handle, and one or more twisted wires secured to the handle and having fixed filaments between turns of the wire or wires for allowing the interproximal toothbrushes to be suitably inserted or engaged into the interdental spaces between the teeth with the handles.

However, similarly, the interdental toothbrushes of greater sizes or diameters may be inadvertently forced or inserted or engaged into the interdental spaces having relatively smaller sizes or widths, and the gum of the user may also have a good chance to be hurt or injured by the interdental toothbrushes. In addition, the twisted wires may also have a good chance to hurt or injure the gum of the user when the twisted wires of the interdental toothbrushes are not precisely engaged into the interdental spaces between the teeth.

The present invention has arisen to mitigate and/or obviate the afore-described disadvantages of the conventional interdental toothbrushes.

SUMMARY OF THE INVENTION

The primary objective of the present invention is to provide an interdental toothbrush including a gage for guiding the interdental toothbrush to be inserted or engaged into the predetermined or suitable interdental spaces between the teeth and for preventing the interdental toothbrushes of greater sizes or diameters from being inserted or engaged into the interdental spaces having relatively smaller sizes or widths.

In accordance with one aspect of the invention, there is provided an interdental toothbrush comprising at least one wire including a first end portion and a second end portion, and including filaments disposed thereon, and a gage disposed on the second end portion of the wire and including an outer diameter corresponding to that of the filaments for guiding and limiting the wire and the filaments to engage into a predetermined or suitable interdental space between the teeth of a user and for preventing the filaments from being inserted and engaged into an interdental space having a relatively smaller width and for preventing the user's gum from being hurt or injured by the filaments.

The gage includes an outer diameter equal to or slightly smaller than that of the filaments, and is preferably made of soft or rubber or plastic or synthetic or resilient materials for engaging with the user's gum and for preventing the user's gum from being hurt and injured by the wire.

The wire includes a wire segment provided thereon and located between the gage and the filaments. The gage includes a rounded structure or a spherical structure for further preventing the user's gum from being hurt and injured by the wire.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
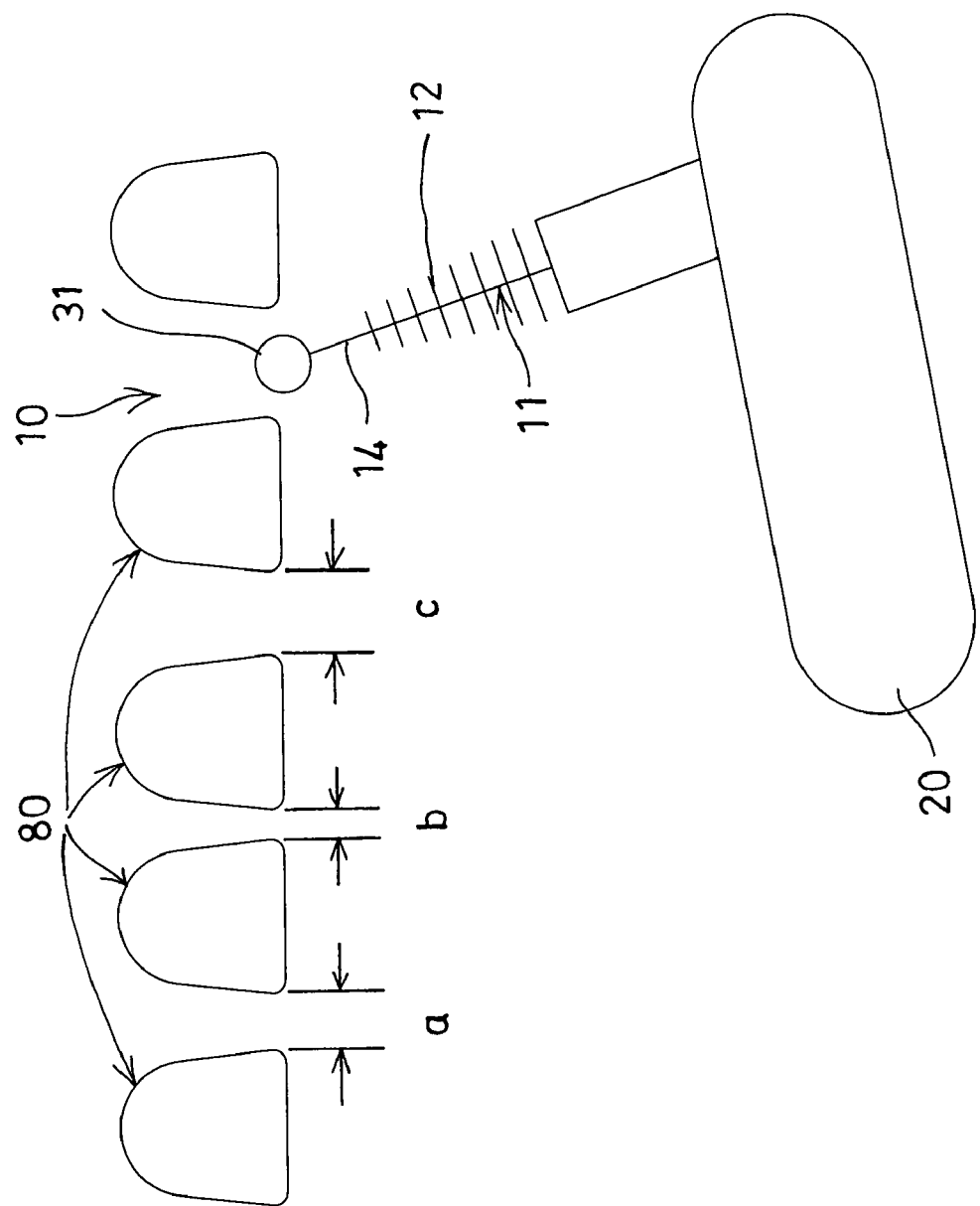
FIG. 1 is a partial perspective view illustrating the operation of an interdental toothbrush in accordance with the present invention for being inserted or engaged into the interdental spaces between the teeth of the user.
Figure 2:
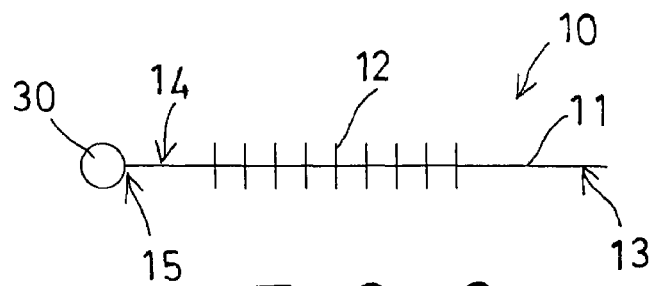
FIG. 2 is a partial plan schematic view illustrating one of the interdental toothbrushes.
Figure 3:
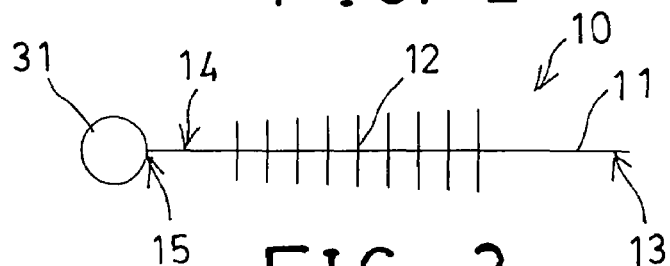
FIG. 3 is a partial plan schematic view similar to FIG. 2, illustrating the other interdental toothbrush.

Referring to the drawings, and initially to FIGS. 1 and 2, an interdental toothbrush 10 in accordance with the present invention also comprises one or more twisted wires 11 having fixed filaments 12 disposed or attached between turns of the wire or wires 11 for inserting or engaging into the interdental spaces a or b or c (FIG. 1) between the teeth 80 of the user and particularly designed for cleaning the hard-to-reach interdental spaces a or b or c between the teeth of the users. The filaments 12 may also be formed into or selected from various kinds of different shapes or contours or sizes or diameters, such as the ultra fine cylindrical shapes (FIG. 2), the ultra fine tapered shapes (FIG. 3), the cylindrical shapes (FIG. 4), the tapered shapes (FIG. 5), the large cylindrical shapes (FIG. 6), or the like.

Figure 5:
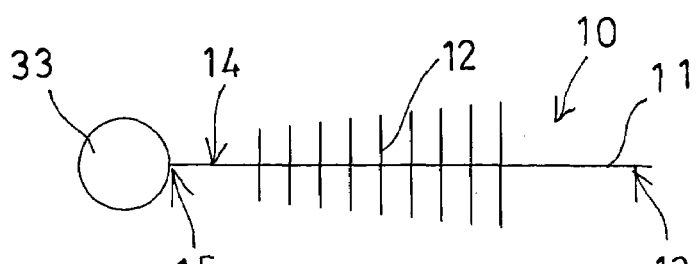
FIG. 5 is a partial plan schematic view similar to FIGS. 2-4, illustrating the still further interdental toothbrush.
Figure 6:
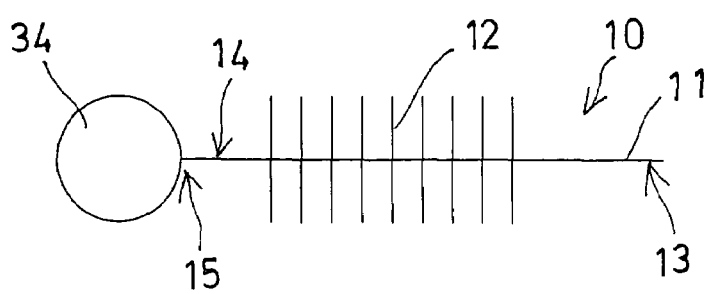
FIG. 6 is a partial plan schematic view similar to FIGS. 2-5, illustrating the still further interdental toothbrush.

For example, the filaments 12 of the ultra fine cylindrical shapes (FIG. 2) may include a size or diameter smaller than that of the cylindrical shapes (FIG. 4) which may include a size or diameter smaller than that of the large cylindrical shapes (FIG. 6). Similarly, the filaments 12 of the ultra fine tapered shapes (FIG. 3) may include a size or diameter smaller than that of the tapered shapes (FIG. 5). Normally, in one refill package of the interproximal toothbrushes, either or some or all of the brushes or refills or toothbrushes 10 of that shown in FIGS. 2-6 may include different shapes or sizes or diameters and may be selectively provided and contained in the package.

The first or rear end portion 13 of the wires 11 may be attached to such as a handle 20 (FIG. 1), or a power or motor-driven device (not shown), or the like which may be used for suitably inserting or engaging the wire or wires 11 and the filaments 12 into either of the interdental spaces a or b or c between the teeth 80 of the user and for moving or actuating the filaments 12 to clean the interdental spaces between the teeth of the users. The handle 20 or the power or motor-driven device (not shown), or the like are not related to the present invention and will not be described in further details. The wire or wires 11 and the filaments 12 are typical and will not be described in further details.

The interdental toothbrush 10 in accordance with the present invention further includes a wire segment 14 selectively, but not necessarily formed or extended or provided on the second or front end portion 15 of each of the wires 11 and having no filaments formed or provided thereon, and a gage 30, 31, 32, 33, 34 disposed or attached to the front portion 15 of each of the wires 11 or of the wire segment 14 of each of the wires 11 and arranged for allowing the wire segment 14 to be formed and provided or located between the gages 30-34 and the filaments 12. The gages 30-34 are preferably made of soft or rubber or plastic or resilient or other synthetic materials and includes a rounded or spatial or three dimensional or spherical structure for safely engaging with the user's gum and for safely inserting or guiding the wire or wires 11 and the filaments 12 to engage into the interdental spaces a or b or c between the teeth 80 and thus for preventing the gum of the user from being hurt or injured by the wire or wires 11.

The gages 30-34 each include a size or outer diameter equal to or slightly smaller than or corresponding to that of the respective filaments 12 for limiting or guiding the interdental toothbrushes 10 to be inserted or engaged into the predetermined or suitable interdental spaces a or b or c between the teeth 80 and for preventing the interdental toothbrushes 10 of greater sizes or diameters from being inserted or engaged into the interdental spaces a or b or c having relatively smaller sizes or widths. For example, the gages 30-31 (FIGS. 2, 3) may be inserted or engaged into all of the interdental spaces a, b, c, but the other greater interdental toothbrushes 10 (FIGS. 4-6) may be prevented from being inserted or engaged into the relatively smaller interdental space b by the gages 32-34.

Figure 4:
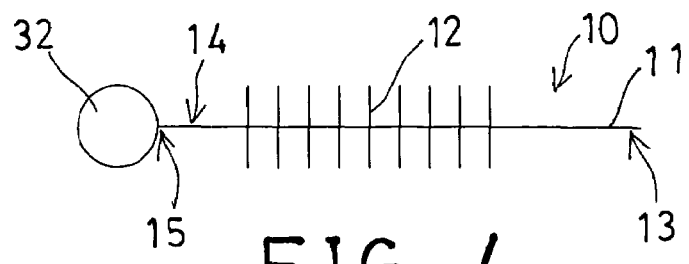
FIG. 4 is a partial plan schematic view similar to FIGS. 2 and 3, illustrating the further interdental toothbrush.

Similarly, the interdental toothbrushes 10 as shown in FIGS. 4-6 may be limited and guided to be inserted or engaged into the relatively greater interdental spaces a, c, except the relatively smaller interdental space b by the gages 32-34, and the greatest gage 34 may limit and guide the interdental toothbrushes 10 as shown in FIG. 6 to engage into the greatest interdental spaces c only but not the relatively smaller interdental spaces a and b, or the greatest gage 34 may limit and prevent the interdental toothbrushes 10 as shown in FIG. 6 from being inserted or engaged into the relatively smaller interdental spaces a and b.

Accordingly, the interdental toothbrushes 10 may be limited and guided to be inserted or engaged into only the predetermined or suitable or relatively greater interdental spaces between the teeth, and may prevent the interdental toothbrushes 10 of greater sizes or diameters from being inserted or engaged into the interdental spaces having relatively smaller sizes or widths, and thus may prevent the gum of the user from being hurt or injured by the filaments 12 having relatively greater sizes or diameters. In addition, the rounded or spatial or three dimensional or spherical gages 30-34 may also prevent the gum of the user from being hurt or injured by the wire or wires 11.

Accordingly, the interdental toothbrush in accordance with the present invention includes a gage for guiding the interdental toothbrush to be inserted or engaged into the predetermined or suitable interdental spaces between the teeth and for preventing the interdental toothbrushes of greater sizes or diameters from being inserted or engaged into the interdental spaces having relatively smaller sizes or widths.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. An interdental toothbrush comprising:
    at least one wire including a first end portion and a second end portion, and including filaments disposed thereon, and
    a gage disposed on said second end portion of said at least one wire and including an outer diameter substantially equal to that of said filaments for limiting said at least one wire and said filaments to engage into a predetermined interdental space between teeth of a user and for preventing said filaments from being inserted and engaged into an interdental space having a relatively smaller width and for preventing the user's gum from being hurt or injured by said filaments.

2. The interdental toothbrush as claimed in claim 1, wherein said at least one wire includes a wire segment provided thereon and located between said gage and said filaments.

3. The interdental toothbrush as claimed in claim 1, wherein said gage includes an outer diameter equal to that of said filaments.

4. The interdental toothbrush as claimed in claim 1, wherein said gage includes an outer diameter smaller than that of said filaments.

5. The interdental toothbrush as claimed in claim 1, wherein said gage is made of soft materials for preventing the user's gum from being hurt and injured by said at least one wire.

6. The interdental toothbrush as claimed in claim 1, wherein said gage includes a rounded structure.

7. The interdental toothbrush as claimed in claim 1, wherein said gage includes a spherical structure.

* * * * *